United States Patent
Davies et al.

(10) Patent No.: US 10,118,874 B2
(45) Date of Patent: Nov. 6, 2018

(54) PROCESS FOR PRODUCING BENZENE FROM A C5-C12 HYDROCARBON MIXTURE

(71) Applicant: SABIC GLOBAL TECHNOLOGIES B.V., Bergen op Zoom (NL)

(72) Inventors: Andrew Davies, Cleveland (GB); Dustin Fickel, Houston, TX (US); Maikel Van Iersel, Den Bosch (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/318,136

(22) PCT Filed: Jun. 1, 2015

(86) PCT No.: PCT/EP2015/062080
§ 371 (c)(1),
(2) Date: Dec. 12, 2016

(87) PCT Pub. No.: WO2015/189058
PCT Pub. Date: Dec. 17, 2015

(65) Prior Publication Data
US 2017/0129828 A1 May 11, 2017

(30) Foreign Application Priority Data

Jun. 13, 2014 (EP) .................................. 14172342

(51) Int. Cl.
*C07C 4/06* (2006.01)
*C10G 47/02* (2006.01)
(Continued)

(52) U.S. Cl.
CPC ................. *C07C 4/06* (2013.01); *B01J 21/04* (2013.01); *B01J 23/42* (2013.01); *B01J 29/40* (2013.01);
(Continued)

(58) Field of Classification Search
None
See application file for complete search history.

(56) References Cited

U.S. PATENT DOCUMENTS

| 3,433,848 A | 3/1969 | Devins et al. |
| 3,517,078 A | 6/1970 | Simonetta |

(Continued)

FOREIGN PATENT DOCUMENTS

| CN | 101734986 A | 6/2010 |
| EP | 0308096 A | 3/1989 |

(Continued)

OTHER PUBLICATIONS

Baerlocher et al.; "Atlas of Zeolite Framework Types"; Elsevier, Fifth Revised Edition, 2001, pp. 1-308.
(Continued)

*Primary Examiner* — Philip Y Louie
(74) *Attorney, Agent, or Firm* — Cantor Colburn LLP

(57) ABSTRACT

The invention relates to a process for producing benzene, comprising the steps of: (a) providing a hydrocracking feed stream comprising C5-C12 hydrocarbons, (b) contacting the hydrocracking feed stream in the presence of hydrogen with a hydrocracking catalyst comprising 0.01-1 wt-% hydrogenation metal in relation to the total catalyst weight and a zeolite having a pore size of 5-8 Å and a silica (SiO2) to alumina (Al$_2$O$_3$) molar ratio of 5-200 under process conditions including a temperature of 425-580° C., a pressure of 300-5000 kPa gauge and a Weight Hourly Space Velocity of 0.1-15 h$^{-1}$ to produce a hydrocracking product stream comprising benzene, toluene and C8+ hydrocarbons, (c) separating benzene, toluene and the C8+ hydrocarbons from the hydrocracking product stream and (d) selectively recycling back at least part of the toluene from the separated products of step (c) to be included in the hydrocracking feed stream
(Continued)

process for producing benzene from a c5-c12 hydrocarbon mixture

13 Claims, 1 Drawing Sheet

(51) Int. Cl.

| | | |
|---|---|---|
| *B01J 29/40* | (2006.01) | |
| *B01J 29/44* | (2006.01) | |
| *C10G 45/62* | (2006.01) | |
| *C10G 45/64* | (2006.01) | |
| *C10G 45/70* | (2006.01) | |
| *C10G 47/00* | (2006.01) | |
| *C10G 47/14* | (2006.01) | |
| *C10G 47/18* | (2006.01) | |
| *C10G 63/00* | (2006.01) | |
| *C10G 63/08* | (2006.01) | |
| *B01J 37/04* | (2006.01) | |
| *B01J 35/00* | (2006.01) | |
| *B01J 21/04* | (2006.01) | |
| *B01J 23/42* | (2006.01) | |

(52) U.S. Cl.
CPC ........... *B01J 29/44* (2013.01); *B01J 35/0006* (2013.01); *B01J 37/04* (2013.01); *C10G 45/62* (2013.01); *C10G 45/64* (2013.01); *C10G 45/70* (2013.01); *C10G 47/00* (2013.01); *C10G 47/14* (2013.01); *C10G 47/18* (2013.01); *C10G 63/00* (2013.01); *C10G 63/08* (2013.01); *C07C 2529/44* (2013.01); *C10G 2300/1044* (2013.01); *C10G 2300/301* (2013.01); *C10G 2300/4056* (2013.01); *C10G 2300/4081* (2013.01); *C10G 2300/708* (2013.01); *C10G 2400/30* (2013.01); *Y02P 20/52* (2015.11)

(56) References Cited

U.S. PATENT DOCUMENTS

| | | | |
|---|---|---|---|
| 3,625,879 | A | 12/1971 | Horne et al. |
| 3,729,409 | A | 4/1973 | Chen |
| 3,957,621 | A | 5/1976 | Bonacci et al. |
| 4,463,206 | A | 7/1984 | Derrien et al. |
| 5,321,183 | A | 6/1994 | Chang et al. |
| 5,792,338 | A | 8/1998 | Gosling et al. |
| 6,001,241 | A | 12/1999 | Golsing et al. |
| 6,619,724 | B2 | 9/2003 | Blomeling et al. |
| 7,297,831 | B2 | 11/2007 | Lee et al. |
| 7,563,358 | B2 | 7/2009 | Stavens et al. |
| 8,168,844 | B2 | 5/2012 | Arca et al. |
| 2006/0287561 | A1 | 12/2006 | Choi et al. |
| 2006/0287564 | A1 | 12/2006 | Choi et al. |
| 2007/0112237 | A1 | 5/2007 | Lee et al. |
| 2008/0051615 | A1 | 2/2008 | Stavens et al. |
| 2009/0272672 | A1 | 11/2009 | Arca et al. |
| 2015/0166434 | A1 | 6/2015 | Ward |

FOREIGN PATENT DOCUMENTS

| | | |
|---|---|---|
| EP | 1564199 A1 | 8/2005 |
| JP | 1967023570 A | 9/1965 |
| JP | S496300 B1 | 2/1974 |
| WO | 0244306 A1 | 6/2002 |
| WO | 2007055488 A1 | 5/2007 |
| WO | 2008015027 A1 | 2/2008 |
| WO | 2010102712 A2 | 9/2010 |
| WO | 2013182534 A1 | 12/2013 |
| WO | 2015128317 A1 | 9/2015 |
| WO | 2016005105 A1 | 1/2016 |

OTHER PUBLICATIONS

Bhirud, "Chances for Innovative Processes at the Interface between Refining and Petrochemistry" Proceedings of the DGMK Conference (2002), pp. 115-122.
Chinese Patent No. 101734986; Date of Publication: Jun. 16, 2010; Abstract Only,1 page.
International Search Report for International Application No. PCT/EP2015/062080; dated Aug. 11, 2015; 5 pages.
Kirk-Othmer Encyclopedia of Chemical Technology, "Molecular Sieves," Fifth Edition, vol. 16, (2006), pp. 811-853.
Le Page, "Applied Heterogeneous Catalysis: Design, Manufacture, Use of Solid Catalysts," (1987) Institut Francais due Petrole Publications; pp. 1-7.
Scherzer et al., Hydrocracking Science and Technology (1996) pp. 13-14 and 174.
Written Opinion of the International Search Report for International Application No. PCT/EP2015/062080; dated Aug. 11, 2015; 7 pages.
Etsuro Nakamura et al., "Studies of C6 to C10 Alkylbenzenes in Crude Oils, Naphthas, Reformates and Cracked Gasolines"; Oil Journal, 1966, vol. 9, No. 8, pp. 634-642 (42-50).
International Search Report for International Application No. PCT/EP2013/061425; International Filing Date: Jun. 4, 2013; dated Aug. 23, 2013; 5 Pages.
Karge et al., "Molecular Sieves: Science and Technology," vol. 3, (2002) pp. 204-255.
Kirk-Othmer Encyclopedia of Chemical Technology "BTX Processing" in ECT 3rd ed., vol. 4, pp. 264-277, by D. L. Ransley, Chevron, Research Company; in ECT 4th ed., vol. 4, pp. 590-605, by W. A. Sweeney and P. F. Bryan, Chevron Research and Technology Company—Publication Dates: Dec. 14, 2007 and Sep. 8, 2010; 17 pages.
Kirk-Othmer Encyclopedia of Chemical Technology, "Fuels, Synthetic Liquid" in ECT 1st ed., vol. 6, pp. 960-983, by J. H. Arnold et al., Hydrocarbon Research, Inc.; Sep. 8, 2010; Carbon Monoxide—Hydrogen Reactions in ECT 2nd ed., vol. 4, pp. 446-489, by H. Pichler et al.; Dec. 4, 2000; ECT 3rd ed., vol. 11, pp. 447-489, by C. D. Kalfadelis and H. Shaw, Exxon Research and Engineering Co., Sep. 8, 2010; 42 Pages.
Kirk-Othmer Encyclopedia of Chemical Technology; "Benzene"; vol. 3, 2004, pp. 596-624.
Kirk-Othmer Encyclopedia of Chemical Technology; "Petroleum Refinery Processes"; vol. 18, 2006, 49 Pages.
Meyers "Handbook of Petroleum Refining Processes," (1986) McGraw-Hill: Chemical Process Technology Handbook Series; pp. 1-9.
Mowry, J.R. "UOP Thermal Hydrodealkylation (THDA) Process"; Chapter 2.1; 5 Pages 1986.
Rase, "Handbook of Commercial Catalysts: Heterogeneous Catalysts," (2000) CRC Press LLC, pp. 1-11.
Rase, Handbook of Commercial Catalysts: Heterogeneous Catalysts ed. (2000) CRCPRess p. 211-212.
Scherzer, et al.; "Hydrocracking Science and Technology." (1996) pp. 1-3 (German Language Attached).
Written Opinion of the International Searching Authority for International Application No. PCT/EP2013/061425; International Filing Date: Jun. 4, 2013; dated Aug. 23, 2013; 6 Pages.
Yamazaki., "Determination of Aromatic Hydrocarbons in Petroleum Preparation by HPLC," Central Customs Laboratory, Ministry of France, 2000, No. 39, pp. 67-69.

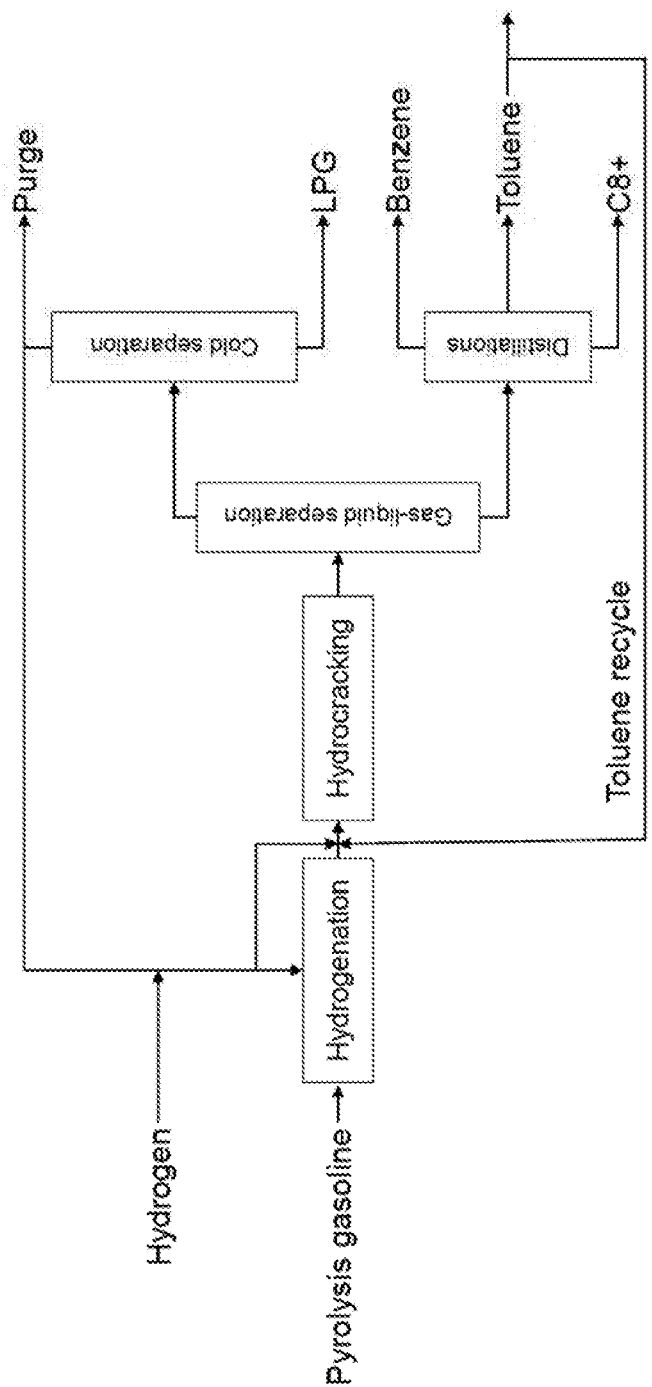

PROCESS FOR PRODUCING BENZENE FROM A C5-C12 HYDROCARBON MIXTURE

CROSS REFERENCE TO RELATED APPLICATIONS

This application is a 371 of International Application No. PCT/EP2015/062080, filed Jun. 1, 2015, which claims priority to European Application No. 14172342.9, filed Jun 13, 2014 both of which are incorporated herein by reference in their entirety.

The present invention relates to a process for producing benzene from a mixed feedstream comprising C5-C12 hydrocarbons by contacting said feedstream in the presence of hydrogen with a catalyst having hydrocracking activity.

WO2013/182534 discloses a process for producing BTX (benzene, toluene and xylene) from a C5-C12 hydrocarbon mixture using a hydrocracking/hydrodesulphurisation catalyst. According to WO2013/182534, the process results in a mixture comprising substantially no co-boilers of BTX, thus chemical grade BTX can easily be obtained.

While the process of WO2013/182534 advantageously limits the amount of BTX co-boilers in the obtained mixture, control of the ratio between benzene, toluene and xylene in the obtained mixture is limited. In some cases, it is preferred to obtain more benzene in the product than was present in the feed and/or to eliminate any benzene losses through the process. WO2013/182534 also mentions separating the BTX from the mixture and contacting the separated BTX with hydrogen under conditions suitable to produce a hydrodealkylation product stream comprising benzene and fuel gas. This results in a high benzene yield, but requires two reactors in series, as hydrocracking and hydrodealkylation is performed under different reaction conditions The use of more reactors typically leads to a higher capital expenditure (CAPEX).

CN101734986 discloses a method for pyrolysing C7+ hydrocarbons in the presence of a catalyst for obtaining a product stream rich in benzene and xylene. CN101734986 mentions that the obtained product stream comprises a large quantity of toluene, as well as heavy hydrocarbons (C9+) and non-aromatic hydrocarbons which are of less value. According to CN101734986, the heavy hydrocarbons (C9+) are recycled back into the reaction zone. In some cases, toluene is also recycled back. The recycling of these materials improves the benzene and xylene yield.

US2006/0287564 describes a process for increasing the production of benzene from a hydrocarbon mixture including separating a hydrocarbon feedstock into a C6 or lower hydrocarbon stream and a C7 or higher hydrocarbon stream. The C6 or lower hydrocarbon stream is separated into a non-aromatic hydrocarbon stream and an aromatic hydrocarbon stream through a solvent extraction process. The C7 or higher hydrocarbon stream is subjected to a reaction in the presence of a catalyst comprising platinum/tin or platinum/lead.

U.S. Pat. No. 3,957,621 describes a process for processing heavy reformates from which benzene and lighter components have been largely removed. The removed stream (overhead stream at line 12 of FIG. 1) includes the major portion of the benzene in the charge and can include a substantial portion of the toluene (col. 4, l.65-69).

It would be desirable to provide a process for converting a C5-C12 hydrocarbon feed stream by which chemical grade benzene is obtained, which results in an increased yield of benzene compared to known processes. It would also be desirable to provide a process which minimizes the capital expenditure required.

It is an object of the present invention to provide a process for converting a C5-C12 hydrocarbon feed stream into a product stream comprising benzene in which the above and/or other needs are met.

Accordingly, the present invention provides a process for producing benzene comprising the steps of:
(a) providing a hydrocracking feed stream comprising C5-C12 hydrocarbons,
(b) contacting the hydrocracking feed stream in the presence of hydrogen with a hydrocracking catalyst comprising 0.01-1 wt-% hydrogenation metal in relation to the total catalyst weight and a zeolite having a pore size of 5-8 Å and a silica ($SiO_2$) to alumina ($Al_2O_3$) molar ratio of 5-200 under process conditions including a temperature of 425-580° C., a pressure of 300-5000 kPa gauge and a Weight Hourly Space Velocity of 0.1-15 $h^{-1}$ to produce a hydrocracking product stream comprising benzene, toluene and C8+ hydrocarbons,
(c) separating benzene, toluene and the C8+ hydrocarbons from the hydrocracking product stream and
(d) selectively recycling back at least part of the toluene from the separated products of step (c) to be included in the hydrocracking feed stream.

The term 'selectively recycle' is herein understood to mean that only toluene is recycled back to be included in the hydrocracking feed stream among the separated products of step (c) comprising benzene, toluene and C8+ hydrocarbons.

Depending on the hydrocracking reaction conditions and the ratio of benzene/toluene/xylene in the hydrocracking feed stream, the conversion of toluene into benzene and xylene (toluene disproportionation) may also occur. In case toluene content of the feed stream is limited, the extent of toluene disproportionation will be limited and hydrocracking will be associated with a benzene loss. By recycling back the toluene separated from the hydrocracking product stream into the hydrocracking feed stream, the benzene to toluene ratio of the hydrocracking feed stream can be manipulated and the extent of the toluene disproportionation can be increased. This leads to an increase in the benzene yield.

Unlike the use of a hydrodealkylation reactor after hydrocracking to convert toluene and xylene to benzene as in WO2013/182534, the benzene yield is increased according to the process of the invention by recycling back of toluene using only hydrocracking reactor. This is beneficial for the reduction of CAPEX. Additionally, toluene disproportionation occurring during the process according to the invention produces significantly lower levels of fuel gas compared to hydrodealkylation.

C8+ hydrocarbons in the hydrocracking product stream comprise xylene. The mild hydrocracking conditions as used according to step b) of the invention result in a product stream comprising benzene, toluene and xylene (BTX), other C8+ hydrocarbons and a low amount of BTX co-boilers. Because of the absence of BTX co-boilers the BTX is a 'chemical grade BTX'. The benzene obtained is a chemical grade benzene. Similarly, the toluene obtained is a chemical grade toluene.

According to the process of the invention, only the toluene is recycled back to be included in the hydrocracking feed stream. This has an advantageous effect on the life time of the hydrocracking catalyst. Heavier hydrocarbons such as C9+ hydrocarbons quickly reduce the life time of the hydrocracking catalyst used in the process of the invention. The hydrocracking feed stream used according to the process of the invention is a lighter feed stream than the feed stream used in the process of CN101734986 that comprises C7+ hydrocarbons. The initial low amount of C9+ components in the feed stream also has an advantageous effect on the life time of the hydrocracking catalyst.

Xylene and the C9+ components in the feed stream will not have beneficial impact on the benzene yield, and can even decrease the benzene yield through e.g. the transalkylation reaction of trimethylbenzene and xylene. Hence, selectively recycling back toluene is advantageous for a higher benzene yield rather than recycling back toluene together with xylene and C9+ components.

As used herein, the term "C# hydrocarbons", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C5+ hydrocarbons" is meant to describe a mixture of hydrocarbons having 5 or more carbon atoms.

The term "BTX" as used herein is well known in the art and relates to a mixture of benzene, toluene and xylenes.

As used herein, the term "chemical grade BTX" relates to a hydrocarbon mixture comprising less than 5 wt-% hydrocarbons other than benzene, toluene and xylenes, preferably less than 4 wt-% hydrocarbons other than benzene, toluene and xylenes, more preferably less than 3 wt-% hydrocarbons other than benzene, toluene and xylenes, and most preferably less than 2.5 wt-% hydrocarbons other than benzene, toluene and xylenes.

Furthermore, the "chemical grade BTX" produced by the process of the present invention comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons. The most critical contaminants are the non-aromatic species which have boiling points close to benzene including, but not limited to, cyclohexane, methylcyclopentane, n-hexane, 2-methylpentane and 3-methylpentane.

Accordingly, the hydrocracking product stream is substantially free from non-aromatic C6+ hydrocarbons. As meant herein, the term "product stream substantially free from non-aromatic C6+ hydrocarbons" means that said product stream comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons.

According to the present invention, chemical grade benzene can also be easily separated from the hydrocracking product stream. As used herein, the term "chemical grade benzene" relates to a hydrocarbon stream comprising less than 0.5 wt % hydrocarbons other than benzene.

According to the present invention, chemical grade toluene can also be easily separated from the hydrocracking product stream. As used herein, the term "chemical grade toluene" relates to a hydrocarbon stream comprising less than 0.5 wt % hydrocarbons other than toluene.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The hydrocracking product stream produced in the process of the present invention preferably comprises less than 10 wt-% of methane. More preferably, the first product stream produced in the process of the present invention comprises less than 5 wt-% of methane, more preferably less than 4 wt-% of methane, more preferably less than 3 wt-% methane, even more preferably less than 2 wt-% methane, particularly preferably less than 1.5 wt-% methane and most preferably less than 1 wt-% methane.

Preferably, the hydrocracking product stream is also substantially free from C5 hydrocarbons. As meant herein, the term "product stream substantially free from C5 hydrocarbons" means that said hydrocracking product stream comprises less than 1 wt-% C5 hydrocarbons, preferably less than 0.7 wt-% C5 hydrocarbons, more preferably less than 0.6 wt-% C5 hydrocarbons and most preferably less than 0.5 wt-% C5 hydrocarbons.

Step a)

According to step a) of the process according to the invention a hydrocracking feed stream comprising C5-C12 hydrocarbons is provided.

Hydrocracking Feed Stream

The hydrocracking feed stream used in the process of the present invention is a mixture comprising C5-C12 hydrocarbons, preferably having a boiling point in the range of 30-195° C. The hydrocracking feed stream comprises the toluene recycled back from the hydrocracking product stream. Preferably, the hydrocracking feed stream mainly comprises C6-C8 hydrocarbons.

Step (a) involves mixing a fresh feed stream and the recycled toluene. The fresh feed stream may comprise at least 10 wt % of benzene, at least 20 wt % of benzene or at least 30 wt % of benzene. Suitable fresh feed streams include, but are not limited to first stage or multi-stage hydro-treated pyrolysis gasoline, straight run naphtha, hydrocracked gasoline, light coker naphtha and coke oven light oil, FCC gasoline, reformate or mixtures thereof.

It is preferred that the non-aromatic species comprised in the hydrocracking feed stream are saturated (e.g. by the prior hydrogenation) in order to reduce the exotherm within the catalyst bed containing the hydrocracking catalyst used in the present process. Accordingly, the hydrocracking feed stream is preferably provided by hydrogenating a source feed stream in a hydrogenation reactor and mixing the hydrogenated source feed stream (fresh feed stream) and the recycled toluene. Suitable source feed streams include, but are not limited to first stage or multi-stage hydro-treated pyrolysis gasoline, straight run naphtha, hydrocracked gasoline, light coker naphtha and coke oven light oil, FCC gasoline, reformate or mixtures thereof. The source feed stream may have a relatively high sulphur content, such as pyrolysis gasoline (pygas), straight run naphtha, light coker naphtha and coke oven light oil and mixtures thereof.

Accordingly, preferably, the fresh feed stream is pyrolysis gasoline, straight run naphtha, light coker naphtha and coke oven light oil or mixtures thereof, optionally after being hydrogenated in a hydrogenation reactor. Preferably, the fresh feed stream has not been subjected to the step of removing benzene.

Preferably, the hydrocracking feed stream has not been subjected to the step of removing benzene. Preferably, the hydrocracking feed stream comprises at least 1 wt % of benzene, for example at least 3 wt %, 5 wt %, 10 wt % or 15 wt %, and/or at most 35 wt %, at most 30 wt %, at most 25 wt % or at most 20 wt %.

Hydrogenation of the source feed stream can be achieved by a hydrogenation reactor in series with the hydrocracking reactor or by a reactor comprising a hydrogenation bed and a hydrocracking bed in series or a layer of a hydrogenation catalyst on top of the hydrocracking catalyst. The single reactor construction would imply lower capital costs compared to two reactors in series.

For instance, a typical composition of first stage hydrotreated pyrolysis gasoline may comprise 10-15 wt-% C5 olefins, 2-4 wt-% C5 paraffins and cycloparaffins, 3-6 wt-% C6 olefins, 1-3 wt-% C6 paraffins and naphthenes, 25-30 wt-% benzene, 15-20 wt-% toluene, 2-5 wt-% ethylbenzene, 3-6 wt-% xylenes, 1-3 wt-% trimethylbenzenes, 4-8 wt-% dicyclopentadiene, and 10-15 wt-% C9+ aromatics, alkylstyrenes and indenes; see e.g. Table E3.1 from Applied Heterogeneous Catalysis: Design, Manufacture, and Use of Solid Catalysts (1987) J. F. Le Page. However, also hydrocarbon mixtures that are depentanised so the concentrations of all the C6 to C9 hydrocarbon species are relatively high compared with the typical figures above can be advantageously used as a feed stream in the process of the present invention.

In one embodiment, the hydrocracking feed stream used in the process of the present invention is treated so that it is enriched in mono-aromatic compounds. As used herein, the term "mono-aromatic compound" relates to a hydrocarbon compound having only one aromatic ring. Means and methods suitable to enrich the content of mono-aromatic compounds in a mixed hydrocarbon stream are well known in the art such as the Maxene process; see Bhirud (2002) Proceedings of the DGMK-conference 115-122. The source feed stream or the hydrocracking feed stream used in the process of the present invention may comprise up to 300 wppm of sulphur (i.e. the weight of sulphur atoms, present in any compound, in relation to the total weight of the feed).

Step b)

According to step b) of the process according to the invention the hydrocracking feed stream is contacted in the presence of hydrogen in a hydrocracking reactor with a hydrocracking catalyst.

The hydrocracking feed stream is contacted with a hydrocracking catalyst in the presence of hydrogen to produce a hydrocracking product stream. During hydrocracking of hydrocarbons, toluene disproportionation influences the proportion of benzene in the product stream:

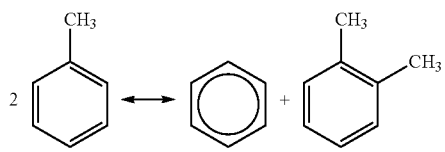

The forward toluene disproportionation reaction increases the amount of benzene. This reaction occurs more in a stream having a low ratio of benzene to toluene.

Recycling back the toluene in step d) of the process of the invention to the hydrocracking feed stream increases the amount of toluene in the hydrocracking feed stream. This results in a higher overall benzene yield compared to the process wherein no recycling back of toluene takes place.

By varying the amount of toluene to be recycled back, the amount of toluene in the hydrocracking feed stream can be controlled. By controlling the amount of toluene in the hydrocracking feed stream, it is advantageously possible to control the amount of benzene in the hydrocracking product stream.

In some embodiments, all of the toluene from the separated products of step (c) is recycled back to be included in the hydrocracking feed stream. In other embodiments, part of the toluene from the separated products of step (c) is recycled back to be included in the hydrocracking feed stream.

Recycling of a higher proportion of toluene increases the benzene yield, but the presence of too much toluene in the hydrocracking feed stream may result in insufficient catalyst activity towards hydrocracking of the benzene coboilers, and hence not to the production of chemical grade benzene. If all of the toluene from the separated products of step (c) is recycled back to be included in the hydrocracking feed stream, the amount of toluene in the hydrocracking feed stream may increase to such an extent that a very large reactor is required for containing enough catalyst to perform both toluene disproportionation as well as benzene purification, i.e. hydrocracking. By limiting the amount of toluene to be recycled, the essential function of benzene purification, i.e. hydrocracking, by the catalyst can be preserved.

Hence, the proportion of the toluene to be recycled back is preferably selected such that there is no benzene loss or a nominal benzene gain during the hydrocracking while sufficient hydrocracking of the benzene coboilers takes place.

Accordingly, the amount of toluene to be included in the hydrocracking feed stream may be set so that there is no benzene loss or a nominal benzene gain. Accordingly, in some embodiments of the process of the invention, the amount of toluene to be recycled back to be included in the hydrocracking feed stream is set so that the proportion of benzene in the hydrocracking product stream is 0-50 mol %, for example 0-25 mol %, for example 0-10 mol %, for example 0-5 wt % higher than the proportion of benzene in the hydrocracking feed stream. This can be achieved by controlling parameter $[BX]/T^2$ described below. The relationship between the $[BX]/T^2$ and the resulting difference in the proportion of benzene in the hydrocracking feed stream and in the hydrocracking product stream can be experimentally determined by the skilled person. The skilled person can accordingly control $[BX]/T^2$ for achieving the desired change in the proportion of benzene in the hydrocracking feed stream and in the hydrocracking product stream.

The toluene in the hydrocracking product stream which is not recycled back to be included in the hydrocracking feed stream may advantageously be subjected to a separate and dedicated toluene disproportionation process reactor or used for other purposes. The use of the dedicated toluene disproportionation reactor further increases the benzene yield. Accordingly, in some embodiments of the present invention, part of the toluene from the separated products of step (c) is contacted with hydrogen under conditions suitable for toluene disproportionation in a reactor separate from the reactor for performing the hydrocracking step (b).

The amount of the toluene to be recycled back to be included in the hydrocracking feed stream may e.g. be 10-80 wt %, for example 50-70 wt % of the toluene in the hydrocracking product stream.

One of the parameters determining the benzene yield from a hydrocracking feed stream comprising BTX and ethylbenzene can be expressed as:

[molar amount of benzene+molar amount of ethylbenzene]*[molar amount of xylene]/[molar amount of toluene]$^2$ (herein sometimes expressed as $[BX]/T^2$)

All amounts in this formula are amounts in the hydrocracking feed stream.

It was found that this parameter can be used as a good indicator for predicting the obtained benzene amount as a result of the toluene disproportionation during hydrocracking. Since it was experimentally found that ethylbenzene is mostly converted to benzene by the hydrocracking step of the invention, the amount of ethylbenzene is added to the amount of benzene in the above formula. Controlling of the $[BX]/T^2$ in the hydrocracking feed stream can easily be done by adjusting the amount of toluene to be recycled. This ensures that a suitable amount of toluene is recycled back for obtaining a good balance between benzene yield and sufficient hydrocracking activity for a reasonably sized reactor with a reasonable CAPEX.

Typically, $[BX]/T^2$ is at most 20, more typically at most 10, more typically at most 5, more typically at most 1. Preferably, $[BX]/T^2$ is at most 0.5, more preferably at most 0.35, more preferably at most 0.25, more preferably at most 0.15. This results in a high benzene yield in the hydrocracking product stream. In order to ensure sufficient hydrocracking activity of the catalyst, $[BX]/T^2$ is preferably higher than zero. Preferably, $[BX]/T^2$ is at least 0.02, for example at least 0.05. The parameter $[BX]/T^2$ may generally be lower for a larger reactor. The range of $[BX]/T^2$ of 0.05 to 0.2 may be optimal for the balance between the good benzene yield and sufficient hydrocracking activity for a reasonably sized reactor with a reasonable CAPEX.

It is noted that U.S. Pat. No. 3,957,621 mentions recycling toluene produced by the hydrocracking to be added to the fresh feed. In table VII of U.S. Pat. No. 3,957,621, the composition of the fresh feed and of the hydrocracking product stream (effluent after the hydrocracking) is shown. The composition of the hydrocracking feed stream, i.e. the mixture of the fresh feed and the recycled toluene to be hydrocracked, is not shown. $[BX]/T^2$ in the hydrocracking feed stream, which is critical for the balance between benzene yield and sufficient hydrocracking activity, is not mentioned in U.S. Pat. Nos. 3,957,621. 3,957,621 does not teach the idea of controlling of the $[BX]/T^2$ in the hydrocracking feed stream. Furthermore, benzene is always removed from the stream to be hydrocracked in U.S. Pat. No. 3,957,621.

Hydrocracking Catalyst

The catalyst according to the invention is a hydrocracking catalyst comprising 0.01-1 wt-% hydrogenation metal and a zeolite having a pore size of 5-8 Å and a silica ($SiO_2$) to alumina ($Al_2O_3$) molar ratio of 5-200 and the process conditions comprise a temperature of 425-580° C., a pressure of 300-5000 kPa gauge and a Weight Hourly Space Velocity of 0.1-15 $h^{-1}$ to produce the hydrocracking product stream.

In preferred embodiments, the hydrocracking catalyst further has a hydrodesulphurisation activity. This is advantageous in that it is not necessary to subject the feed stream to a desulphurisation treatment prior to subjecting said hydrocarbon feed stream to the hydrocracking treatment.

Catalysts Having Hydrocracking/Hydrodesulphurisation Activity ("hydrocracking/hydrodesulphurisation catalyst") are described on pages 13-14 and 174 of Hydrocracking Science and Technology (1996) Ed. Julius Scherzer, A. J. Gruia, Pub. Taylor and Francis. Hydrocracking and hydrodesulphurisation reactions proceed through a bifunctional mechanism which requires a relatively strong acid function, which provides for the cracking and isomerization and which provides breaking of the sulphur-carbon bonds comprised in the organic sulphur compounds comprised in the feed, and a metal function, which provides for the olefin hydrogenation and the formation of hydrogen sulphide. Many catalysts used for the hydrocracking/hydrodesulphurisation process are formed by composting various transition metals with the solid support such as alumina, silica, alumina-silica, magnesia and zeolites.

It is a particular advantage of the process of the invention that the hydrocracking product stream is substantially free from non-aromatic C6+ hydrocarbons as these hydrocarbons usually have boiling points close to the boiling point of C6+ aromatic hydrocarbons. Hence, it can be difficult to separate the non-aromatic C6+ hydrocarbons from the aromatic C6+ hydrocarbons comprised in the hydrocracking product stream by distillation.

These advantageous effects are obtained by strategically selecting the hydrocracking catalyst in combination with the hydrocracking conditions. By combining a hydrocracking catalyst having a relatively strong acid function (e.g. by selecting a catalyst comprising a zeolite having a pore size of 5-8 Å and a silica ($SiO_2$) to alumina ($Al_2O_3$) molar ratio of 5-200) and a relatively strong hydrogenation activity (e.g. by selecting a catalyst comprising 0.01-1 wt-% hydrogenation metal) with process conditions comprising a relatively high process temperature (e.g. by selecting a temperature of 425-580° C.), chemical grade BTX can be produced from a mixed C5-C12 hydrocarbon feed stream, wherein the conversion of the benzene comprised in the feed stream to other hydrocarbon compounds such as naphthene compounds is reduced.

The hydrocracking of the feed stream is performed at a pressure of 300-5000 kPa gauge, preferably at a pressure of 600-3000 kPa gauge, more preferably at a pressure of 1000-2000 kPa gauge and most preferably at a pressure of 1200-1600 kPa gauge. By increasing reactor pressure, conversion of C5+ non-aromatics can be increased, but also increases the yield of methane and the hydrogenation of aromatic rings to cyclohexane species which can be cracked to LPG species. This results in a reduction in aromatic yield as the pressure is increased, and as some cyclohexane and its isomer methylcyclopentane, are not fully hydrocracked, there is an optimum in the purity of the resultant benzene at a pressure of 1200-1600 kPa.

The hydrocracking/hydrodesulphurisation of the feed stream is performed at a Weight Hourly Space Velocity (WHSV) of 0.1-15 $h^{-1}$, preferably at a Weight Hourly Space Velocity of 1-10 $h^{-1}$ and more preferably at a Weight Hourly Space Velocity of 2-9 $h^{-1}$. When the space velocity is too high, not all BTX co-boiling paraffin components are hydrocracked, so it will not be possible to achieve BTX specification by simple distillation of the reactor product. At too low space velocity the yield of methane rises at the expense of propane and butane. By selecting the optimal Weight Hourly Space Velocity, it was surprisingly found that sufficiently complete reaction of the benzene co-boilers is achieved to produce on spec BTX without the need for a liquid recycle.

Accordingly, the hydrocracking conditions thus include a temperature of 425-580° C., a pressure of 300-5000 kPa gauge and a Weight Hourly Space Velocity of 0.1-15 $h^{-1}$. Preferred hydrocracking conditions include a temperature of 450-550° C., a pressure of 600-3000 kPa gauge and a Weight Hourly Space Velocity of 1-10 $h^{-1}$. More preferred hydrocracking conditions include a temperature of 450-550° C., a pressure of 1000-2000 kPa gauge and a Weight Hourly Space Velocity of 2-9 ft'.

Hydrocracking catalysts that are particularly suitable for the process of the present invention comprise a molecular sieve, preferably a zeolite, having a pore size of 5-8 Å.

Zeolites are well-known molecular sieves having a well-defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). Preferably, the hydrocracking catalyst comprises a medium pore size aluminosilicate zeolite or a large pore size aluminosilicate zeolite. Suitable zeolites include, but are not limited to, ZSM-5, MCM-22, ZSM-11, beta zeolite, EU-1 zeolite, zeolite Y, faujastite, ferrierite and mordenite. The term "medium pore zeolite" is commonly used in the field of zeolite catalysts. Accordingly, a medium pore size zeolite is a zeolite having a pore size of about 5-6 Å. Suitable medium pore size zeolites are 10-ring zeolites, i.e. the pore is formed by a ring consisting of 10 $SiO_4$ tetrahedra. Suitable large pore size zeolites have a pore size of about 6-8 Å and are of the 12-ring structure type. Zeolites of the 8-ring structure type are called small pore size zeolites. In the above cited Atlas of Zeolite Framework Types various zeolites are listed based on ring structure. Most preferably the zeolite is ZSM-5 zeolite, which is a well-known zeolite having MFI structure. ZSM-5 zeolite is preferred for the high purity of BTX.

Preferably, the silica to alimuna ratio of the ZSM-5 zeolite is in the range of 20-200, more preferably in the range of 30-100.

The zeolite is in the hydrogen form: i.e. having at least a portion of the original cations associated therewith replaced by hydrogen. Methods to convert an aluminosilicate zeolite to the hydrogen form are well known in the art. A first method involves direct ion exchange employing an acid and/or salt. A second method involves base-exchange using ammonium salts followed by calcination.

Furthermore, the catalyst composition comprises a sufficient amount of hydrogenation metal to ensure that the catalyst has a relatively strong hydrogenation activity. Hydrogenation metals are well known in the art of petrochemical catalysts.

It is preferred that the catalyst does not comprise secondary metals, such as tin, lead or bismuth, that inhibit the hydrogenation activity of the hydrogenation metal. Preferably, the hydrocracking catalyst used in the process of the present invention (the first hydrocracking catalyst and the second hydrocracking catalyst) accordingly comprises less than 0.01 parts tin and less than 0.02 parts lead and less than 0.01 parts bismuth (on the basis of 100 parts by weight of the total catalyst), preferably less than 0.005 parts tin and less than 0.01 parts lead and less than 0.005 parts bismuth (on the basis of 100 parts by weight of total catalyst).

The catalyst composition comprises 0.01-1 wt-% hydrogenation metal, preferably 0.01-0.7 wt-%, more preferably 0.01-0.5 wt-% hydrogenation metal, more preferably 0.01-0.3 wt-%. The catalyst composition may comprise 0.01-0.1 wt-% or 0.02-0.09 wt-% hydrogenation metal. In the context of the present invention, the term "wt %" when relating to the metal content as comprised in a catalyst composition relates to the wt % (or "wt-%") of said metal in relation to the weight of the total catalyst, including catalyst binders, fillers, diluents and the like. Preferably, the hydrogenation metal is at least one element selected from Group 10 of the periodic table of Elements. The preferred Group 10 element is platinum. Accordingly, the hydrocracking catalyst used in the process of the present invention preferably comprises a zeolite having a pore size of 5-8 Å, a silica ($SiO_2$) to alumina ($Al_2O_3$) molar ratio of 5-200 and 0.01-1 wt-% platinum (in relation to the total catalyst).

The hydrocracking catalyst composition may further comprise a binder. Alumina ($Al_2O_3$) is a preferred binder. The catalyst composition of the present invention preferably comprises at least 10 wt-%, most preferably at least 20 wt-% binder and more preferably comprises up to 40 wt-% binder in relation to the total amount of the catalyst. In one embodiment, the hydrogenation metal is deposited on the binder, which preferably is $Al_2O_3$. In some embodiments, the catalyst composition of the present invention comprises little or no binder, for example less than 2 wt %, less than 1 wt %, less than 0.5 wt % or 0 wt %.

According to one embodiment of the invention the hydrocracking catalyst is a mixture of the hydrogenation metal on a support of an amorphous alumina and the zeolite. In this case, the hydrocracking catalyst can be made by physically mixing the zeolite with the amorphous alumina on which the hydrogenation metal is present.

According to another embodiment of the invention the hydrocracking catalyst comprises the hydrogenation metal on a zeolite-based support. In this case, the hydrogenation metal is deposited on the zeolite which acts as a support. The deposition of a hydrogenation metal on a zeolite is well-known and can e.g. be done by wet impregnation, base exchange or ion exchange. The presence of the hydrogenation metal on the zeolite may e.g. be determined by Energy Dispersive X-Ray Spectroscopy (EDS) (through use of SEM), CO chemisorption, inductively coupled plasma atomic emission spectroscopy (ICP-AES) or X-Ray Fluorescence (XRF). In this case, the hydrogenation metal and the zeolite, which gives cracking functionality, are in closer proximity to one another, which translates into a shorter diffusion length between the two sites. This allows high space velocity, which translates into smaller reactor volumes and thus lower CAPEX. Accordingly, in some preferred embodiments, the hydrocracking catalyst is the hydrogenation metal on a support of the zeolite and step (b) is performed at a Weight Hourly Space Velocity of 1-15 or 10-15 $h^{-1}$.

The hydrocracking step is performed in the presence of an excess amount of hydrogen in the reaction mixture. This means that a more than stoichiometric amount of hydrogen is present in the reaction mixture that is subjected to hydrocracking. Preferably, the molar ratio of hydrogen to hydrocarbon species ($H_2$/HC molar ratio) in the reactor feed is between 1:1 and 4:1, preferably between 1:1 and 3:1 and most preferably between 1:1 and 2:1. A higher benzene purity in the product stream can be obtained by selecting a relatively low $H_2$/HC molar ratio. In this context the term "hydrocarbon species" means all hydrocarbon molecules present in the reactor feed such as benzene, toluene, hexane, cyclohexane etc. It is necessary to know the composition of the feed to then calculate the average molecular weight of this stream to be able to calculate the correct hydrogen feed rate. The excess amount of hydrogen in the reaction mixture suppresses the coke formation which is believed to lead to catalyst deactivation.

Step c)

According to step c) of the process according to the invention, benzene, toluene and C8+ hydrocarbons are separated from the hydrocracking product stream.

The hydrocracking product stream comprises methane, LPG, benzene, toluene and C8+ hydrocarbons. The term "LPG" as used herein refers to the well-established acronym for the term "liquefied petroleum gas". LPG generally consists of a blend of C2-C4 hydrocarbons i.e. a mixture of C2, C3, and C4 hydrocarbons. The hydrocracking product stream may be subjected to separation by standard means and methods suitable for separating methane and unreacted hydrogen comprised in the hydrocracking product stream as a first separate stream, the LPG comprised in the hydrocracking product stream as a second separate stream and benzene, toluene and C8+ hydrocarbons as a third separate stream. Preferably, the stream comprising benzene, toluene and C8+ hydrocarbons is separated from the hydrocracking product stream by gas-liquid separation or distillation. One non-limiting example of such a separation method includes a series of distillation steps. The first distillation step at moderate temperature is to separate most of the aromatic species (liquid product) from the hydrogen, $H_2S$, methane and LPG species. The gaseous stream from this distillation is further cooled (to about −30° C.) and distilled again to separate the remaining aromatics species and most of the propane and butane. The gaseous product (mainly hydrogen, $H_2S$, methane and ethane) is then further cooled (to about −100° C.) to separate the ethane and leave the hydrogen, $H_2S$ and methane in the gaseous stream that will be recycled back to the hydrocracking reactor. To control the levels of $H_2S$ and methane in the reactor feed, a proportion of recycle gas stream is removed from the system as a purge. The quantity of material that is purged depends on the levels of methane and $H_2S$ in the recycle stream which in-turn depend on the feed composition. The purge stream will have the same composition as the recycle stream. As the purge will contain mainly hydrogen and methane it is suitable for use as a fuel gas or may be further treated (e.g. via a pressure swing adsorption unit) to separately recover a high purity hydrogen stream and a methane/$H_2S$ stream which can be used as a fuel gas.

Step d)

According to step d) of the process according to the invention, benzene and toluene are separated from the stream of benzene, toluene and C8+ hydrocarbons.

Benzene and toluene are separated from each other by gas-liquid separation or distillation. Chemical grade benzene and chemical grade toluene are obtained.

At least part of the obtained toluene is recycled back to be included in the hydrocracking feed stream. The amount of the toluene that is to be included in the feed hydrocracking stream can be varied in order to optimize the amount of benzene in the hydrocracking product stream.

Xylene may be separated from the C8+ hydrocarbon. Preferably, the separation is done by gas-liquid separation or distillation.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be elucidated by the following non-limiting Examples.

FIGURE shows a scheme illustrating an example of the process according to the invention. In this example, the source feed stream (pyrolysis gasoline) is contacted with hydrogen and treated in a hydrogenation reactor. After the hydrogenation, additional hydrogen is supplied and the hydrogenated stream is combined with the toluene that is recycled back and the hydrocracking feed stream thus obtained is introduced into the hydrocracking reactor (MHC). The hydrocracking product stream is subjected to gas-liquid separation to be separated into a gas phase of hydrogen, methane and LPG and a liquid phase of benzene, toluene and C8+ hydrocarbons. The liquid phase is thereafter separated into benzene, toluene and C8+ hydrocarbons by simple distillation. Part of the toluene obtained is recycled back to be combined with the hydrogenated stream.

EXAMPLES

Feed mixtures comprising different compositions of hydrocarbons were subjected to hydrocracking in order to determine the influence of the feed compositions to the product compositions. The experiments were carried out in a 12 mm reactor, wherein the catalyst bed was located in the isothermal zone of the reactor heater. The catalyst used was 2.0 g of Pt deposited on ZSM-5, wherein $SiO_2/Al_2O_3=50$. The amount of Pt was 0.08 wt % with respect to the total of Pt and ZSM-5. No binder was used in the catalyst.

The feed streams were fed to the reactor. The feed stream enters a vaporizer section prior to the reactor where it is vaporized at 280° C. and mixed with hydrogen gas. The conditions used throughout these experiments were: WHSV=6/hr, pressure was 1379 kPa (200 psig), temperature was 475° C. and the molar ratio $H_2$/hydrocarbons was 3. The effluent of the reactor was sampled in the gas phase to an online gas chromatograph. Product analyses were carried out once per hour.

In experiment 1, different feed streams (Feed 1-5) obtained by adding toluene to pyrolysis gasoline samples were subjected to hydrocracking. The compositions of the feed streams are given in Table 1. The hydrocracking resulted in hydrocracking product streams (Product 1-5) with compositions according to Table 2. By comparing the results in Table 2 it was observed that when the wt % of toluene in the feed stream rises and the $[BX]/T^2$ molar value (the ratio of [the product of the molar amounts of (benzene+ ethylbenzene) and xylene] to [the molar amount of toluene]$^2$) is reduced, the overall benzene yield is increased during hydrocracking. Benzene loss was almost zero at $[BX]/T^2$ of 0.16. A benzene gain was obtained at $[BX]/T^2$ of 0.09.

TABLE 1

Compositions of hydrocracking feed stream

| Component | Feed #1 | Feed #2 | Feed #3 | Feed #4 | Feed #5 |
|---|---|---|---|---|---|
| Benzene (wt %) | 51.64% | 50.14% | 46.75% | 43.28% | 39.86% |
| Toluene (wt %) | 12.73% | 15.64% | 21.39% | 27.35% | 33.13% |
| Ethylbenzene (wt %) | 4.19% | 4.04% | 3.79% | 3.51% | 3.21% |
| BTX (wt %) | 67.35% | 68.64% | 70.80% | 73.10% | 75.25% |
| Total Aromatics (wt %) | 72.11% | 73.20% | 75.08% | 77.06% | 78.86% |
| $[BX]/T^2$ (molar) | 1.03 | 0.64 | 0.30 | 0.16 | 0.09 |

TABLE 2

| Compositions of hydrocracking product stream | | | | | |
|---|---|---|---|---|---|
| Component | Product #1 | Product #2 | Product #3 | Product #4 | Product #5 |
| Benzene (wt %) | 48.29% | 47.25% | 45.28% | 43.17% | 41.28% |
| Toluene (wt %) | 18.78% | 20.42% | 23.47% | 26.56% | 29.35% |
| Ethylbenzene (wt %) | 0.34% | 0.35% | 0.32% | 0.30% | 0.26% |
| BTX (wt %) | 69.89% | 70.86% | 72.62% | 74.50% | 76.23% |
| Total Aromatics (wt %) | 70.84% | 71.83% | 73.64% | 75.46% | 77.17% |
| [BX]/T$^2$ (molar) | 0.41 | 0.39 | 0.34 | 0.31 | 0.29 |
| Benzene Purity (%) | 99.90% | 99.89% | 99.88% | 99.88% | 99.88% |
| Toluene Gain/Loss (%) | +47.52% | +30.56% | +9.72% | −2.89% | −11.41% |
| Toluene Gain/Loss (moles) | +0.066 | +0.052 | +0.023 | −0.009 | −0.041 |
| Benzene Gain/Loss (%) | −6.49% | −5.76% | −3.14% | −0.25% | +3.56% |
| Benzene Gain/Loss (moles) | −0.043 | −0.037 | −0.019 | −0.001 | +0.018 |

Benzene purity is defined as [mass of benzene]/[sum of the masses of benzene, 2-methylpentane, 3-methylpentane, hexane, methylcyclopentane and cyclohexane].

The invention claimed is:

1. A process for producing benzene, comprising the steps of:
   (a) providing a hydrocracking feed stream comprising C5-C12 hydrocarbons,
   (b) contacting the hydrocracking feed stream in the presence of hydrogen with a hydrocracking catalyst comprising 0.01-1 wt-% hydrogenation metal in relation to the total catalyst weight and a zeolite having a pore size of 5-8 Å and a silica (SiO2) to alumina (Al$_2$O$_3$) molar ratio of 5-200 under process conditions including a temperature of 425-580° C., a pressure of 300-5000 kPa gauge and a Weight Hourly Space Velocity of 0.1-15 h$^{-1}$ to produce a hydrocracking product stream comprising benzene, toluene and C8+ hydrocarbons,
   (c) separating benzene, toluene and the C8+ hydrocarbons from the hydrocracking product stream, and
   (d) selectively recycling at least part of the toluene from the separated products of step (c) to the hydrocracking feed stream,
   wherein the amount of toluene to be recycled to the hydrocracking feed stream is set so that the ratio of [molar amount of benzene+molar amount of ethylbenzene]*[molar amount of xylene] divided by [molar amount of toluene]$^2$ in the hydrocracking feed stream is 0.05 to 0.15.

2. The process according to claim 1, wherein step (a) involves mixing a fresh feed stream and the recycled toluene, wherein the fresh feed stream comprises at least 10 wt % benzene.

3. The process according to claim 2, wherein the fresh feed stream is pyrolysis gasoline, straight run naphtha, light coker naphtha, coke oven light oil or mixtures thereof, optionally after being hydrogenated in a hydrogenation reactor.

4. The process according to claim 1, wherein the hydrocracking feed stream has not been subjected to the step of removing benzene.

5. The process according to claim 1, wherein the hydrocracking feed stream comprises at least 1 wt % benzene.

6. The process according to claim 1, wherein the hydrocracking catalyst comprises less than 0.01 parts tin, less than 0.02 parts lead, and less than 0.01 parts bismuth on the basis of 100 parts by weight of the total catalyst.

7. The process according to claim 1, wherein the amount of toluene to be recycled back to the hydrocracking feed stream is set so that the proportion of benzene in the hydrocracking product stream is 0-5 mol % higher than the proportion of benzene in the hydrocracking feed stream.

8. The process according to claim 1, wherein xylene is separated from the hydrocracking product stream.

9. The process according to claim 1, wherein the zeolite is a ZSM-5 zeolite.

10. The process according to claim 1, wherein the hydrogenation metal is platinum.

11. The process according to claim 1, wherein the hydrocracking catalyst comprises the hydrogenation metal on a zeolite-based support.

12. The process according to claim 2, wherein the fresh feed stream comprises at least 20 wt % benzene.

13. The process according to claim 12, wherein the fresh stream comprises at least 30 wt % benzene.

* * * * *